United States Patent [19]

Lachnit-Fixson et al.

[11] 4,145,416

[45] Mar. 20, 1979

[54] NOVEL AGENTS AND NOVEL METHODS FOR TREATMENT OF CLIMACTERIC DISTURBANCES

[75] Inventors: Ursula Lachnit-Fixson; Friedmund Neumann, both of Berlin, Fed. Rep. of Germany

[73] Assignee: Schering, A.G., Berlin and Bergkamen, Fed. Rep. of Germany

[21] Appl. No.: 837,323

[22] Filed: Sep. 27, 1977

Related U.S. Application Data

[63] Continuation-in-part of Ser. No. 699,192, Jun. 23, 1976, Pat. No. 4,076,811.

[30] Foreign Application Priority Data

Oct. 5, 1976 [DE] Fed. Rep. of Germany ....... 2645307

[51] Int. Cl.$^2$ .......................... A61K 31/56; C07J 9/00
[52] U.S. Cl. ................................ 424/238; 260/397.5; 424/239
[58] Field of Search .................... 260/397.5; 424/239, 424/238

[56] References Cited

U.S. PATENT DOCUMENTS

| | | | |
|---|---|---|---|
| 3,639,599 | 2/1972 | Mehrhof et al. | 424/239 |
| 3,932,635 | 1/1976 | Segre | 424/239 |

*Primary Examiner*—Elbert L. Roberts
*Assistant Examiner*—Robert C. Whittenbaugh
*Attorney, Agent, or Firm*—Millen & White

[57] ABSTRACT

Relief from climacteric disturbances is achieved by administration of first a combination of an estrogen of type 1 and an estrogen of type 2, approximately in a ratio of 2:1 to 1:8, daily over 10–12 days; then a combination of an estrogen of type 1 and an estrogen of type 2, approximately in a ratio of 2:1 to 1:8, and a progestogen, daily over 9–11 days; and thereafter an estrogen of type 2, or a placebo, daily over 6–8 days.

23 Claims, No Drawings

NOVEL AGENTS AND NOVEL METHODS FOR TREATMENT OF CLIMACTERIC DISTURBANCES

This is a continuation-in-part of application Ser. No. 699,192, filed June 23, 1976 now U.S. Pat. No. 4,076,811.

BACKGROUND OF THE INVENTION

This invention relates to novel agents and novel methods for the treatment of climacteric disturbances.

In the past, climacteric changes have been treated with a great variety of estrogens. For example, typical climacteric complaints, such as hot flashes and outbreaks of perspiration, insomnia, cardiovascular sensations, and sensations of dizziness can be eliminated by the daily administration of estradiol valerate for 21 days, followed by a subsequent seven-day hormone-free phase.

Psychic changes, manifesting themselves by emotional imbalance can likewise be eliminated by administration of estradiol valerate. A disadvantage of using estradiol valerate is that the treatment results in extensive proliferation of the endometrium, which leads, in turn, to undesirable uterine bleeding. The strong effect of estradiol valerate on the upper genital tract also limits the use of this compound.

Furthermore, treatment of climacteric disturbances with estriol is conventional. Estriol has a favorable effect on the lower genital tract (cervix uteri, vagina, and vulva), but has the disadvantage that typical complaints and psychic changes are not fully satisfactorily ameliorated.

The effects on the above climacteric symptoms can be increased and the effect on the uterus can be extensively eliminated by the use of a suitable combination of natural estrogens. Since considerable synergism in ameliorating the symptoms is observed simultaneously with an antagonistic effect on the side effects, another advantage is obtained in that the estrogens can be employed in relatively low dosages.

Estradiol and the derivatives thereof can be utilized as natural estrogens having a strong effect on the disturbances and on the upper genital tract. Such derivatives are conventionally understood to include compounds produced by esterification or etherification of estradiol. Preferably suitable are esters of estradiol, such as estradiol valerate (type 1).

Suitable natural estrogens having a minor effect on the disturbances and a strong effect on the lower genital tract are estriol and the derivatives thereof. Such derivatives are conventionally understood to include especially ethers and esters of estriol. Well suitable, for example, are estriol and estriol succinate (type 2). A reliable effect is obtained by administering a combination of a natural estrogen of type 1 (estradiol or derivatives of estradiol) and a natural estrogen of type 2 (estriol or a derivative of estriol) approximately in a ratio of from 2:1 to 1:8 over a period of 21 days and subsequently administering solely a natural estrogen of type 2, or no hormones at all, over a period of 7 days. By spreading the dosage over 28 days, an adaptation to the normal female cycle is obtained. (See U.S. application Ser. No. 699,192 filed on June 23, 1976, now U.S. Pat. No. 4,076,811, whose disclosure is incorporated by reference.).

However, all such prior treatments are not fully satisfactory. For example, a disadvantage inherent in pure estrogen therapy is the danger of a nonphysiological proliferation at the endometrium and the tissue of the mammary gland.

SUMMARY OF THE INVENTION

Accordingly, it is an object of the present invention to provide a composition and method for treating climacteric disturbances.

It is a further object to provide such a composition and method which lessens the danger of non-physiological proliferation at the endometrium and tissue of the mammary gland.

It has now been discovered that the residual effect of estrogens on the uterus and mammae can be rendered harmless by additionally administering a progestational agent in the second half of the cycle over a period of 9-11 days. The addition of the progestogen effects a transformation of the endometrium and a cyclic menstrual flow.

In a composition aspect, this invention relates to a combination of novel agents for the treatment of climacteric disturbances to be administered in three phases consisting of:

for the first phase, 10-12 dosage units of a combination of an estrogen of type 1 and an estrogen of type 2, approximately in a weight ratio of from 2:1 to 1:8, preferably in a ratio of about 1:2;

for the second phase, 9-11 dosage units of a combination of an estrogen of type 1 and an estrogen of type 2, approximately in a weight ratio of from 2:1 to 1:8, preferably in a ratio of about 1:2, and a progestational agent;

for the third phase, 6-8 dosage units in the form of an estrogen of type 2, or no hormones at all; and carriers, flavor-ameliorating agents, fillers and/or other adjuvants conventional in galenic pharmacy.

The total number of dosage units of the first, second and third phases is to be 28 in all instances, providing 28 daily dosages. The dosage units of the third phase can also be free of hormone, i.e., a placebo can be administered.

In a method of use aspect, this invention also relates to a novel method for the treatment of climacteric disturbances, which comprises administering first, a combination of an estrogen of type 1 and an estrogen of type 2 approximately in a weight ratio of from 2:1 to 1:8, preferably in a ratio of about 1:2, once daily over a period of 10-12 days; then a combination of an estrogen of type 1 and an estrogen of type 2 approximately in a weight ratio of from 2:1 to 1:8, preferably in a ratio of about 1:2, and a progestational agent, once daily over a period of 9-11 days; and thereafter an estrogen of type 2 or no hormones at all, once daily over a period of 6-8 days.

DETAILED DISCUSSION

Suitable estrogens of type 1 include, in particular, estradiol and esters of estradiol, such as estradiol valerate and benzoate. Other conventional estrogens of type 1 can also be used. The amount of estrogen of type 1 utilized daily in accordance with this invention should be that amount which corresponds to the daily administration of 0.5 - 4 mg. of estradiol valerate.

Especially suitable as estrogens of type 2 include estriol and esters of estriol, such as estriol succinate. Other conventional estrogens of type 2 can also be used. The amount of estrogen of type 2 utilized daily according to this invention should be that amount which corresponds to the daily administration of 0.5 – 8 mg. of estriol.

All progestationally active compounds are suitable as the progestogen component according to the present invention. The progestogen employed should be contained in the formulation in amounts preferably corresponding to a daily dose of from 0.1 – 0.5 mg. of D-norgestrel, independent of the amounts of estrogens of type 1 or type 2. Suitable as the progestogen component are, inter alia, progesterone, 17-hydroxyprogesterone esters, 19-nor-17-hydroxyprogesterone esters, 17α-ethynyltestosterone, 17α-ethynyl-19-nortestosterone (norethisterone), 17α-ethynyl-18-methyl-19-nortestosterone (D-norgestrel) and suitable derivatives thereof. Such derivatives are conventionally understood to include compounds formed by the introduction of double bonds or substituents or by esterification, etherification, ketalization, etc.

Additional double bonds can be present, inter alia, in the 1,2-, 6,7-, 15,16- or 16,17-position. Suitable substituents include halogen atoms, especially fluorine or bromine atoms, methyl, hydroxy, methoxy and acetoxy groups in the 4-, 6-, 7-, 11- and/or 16-positions; and methylene groups in the 1,2-, 6,7-, 15,16- and/or 16,17-positions. The 3-keto group of the progestogens can be reduced or eliminated. The 4,5-double bond can be shifted to the 5,6- or 5,10-position. Suitable esters include the esters of those acids conventionally employed in steroid chemistry for esterifying the steroid alcohols, for example, alkanecarboxylic acids, particularly of 1-11 carbon atoms. Examples of suitable ethers include alkyl ethers and tetrahydropyranyl ethers; and suitable ketals include those of ethanediol and of the propanediols.

Preferred progestogens are D-norgestrel, norethisterone acetate and cyproterone acetate (17-acetoxy-6-chloro-1α,2α-methylene-4,6-pregnadiene-3,20-dione).

The active components are preferably given together orally, but they can also be administered separately or parenterally. For this purpose, the active agents are conventionally processed, together with additives, carriers, flavor ameliorating agents and/or other adjuvants conventional in galenic pharmacy, into the customary forms of application by known methods. For the preferred oral administration, especially suitable are tablets, dragees, capsules, pills, suspensions or solutions; and for parenteral application, oily solutions are particularly preferred, such as, for example, sesame oil or caster oil solutions which can also additionally contain a diluent, for example benzyl benzoate or benzyl alcohol.

For the preferred oral application, the three-phase agents are suitably provided in the form of a package. Accordingly, the invention furthermore relates to packages, characterized in that they contain 28 dosage units for oral administration in a synchronized, fixedly determined sequence, wherein the sequence corresponds to the phases of daily administration. The package can be fashioned, inter alia, in the form of a blister package with, for example, 11 dragees of the first phase, 10 dragees of the second phase, and 7 dragees of the third phase, from which respectively one dragee per day can be withdrawn over a period of 28 days.

Without further elaboration, it is believed that one skilled in the art can, using the preceding description, utilize the present invention to its fullest extent. The following preferred specific embodiments are, therefore, to be construed as merely illustrative and not limitative of the remainder of the disclosure in any way whatsoever.

EXAMPLE 1

| | (Composition of a Dragee for Each Phase) | |
|---|---|---|
| 1st Phase: (11 Dragees) | 1.000 mg. | Estradiol valerate |
| | 2.000 mg. | Estriol |
| | 43.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 2nd Phase: (10 Dragees) | 1.000 mg. | Estradiol valerate |
| | 2.000 mg. | Estriol |
| | 0.250 mg. | D-Norgestrel |
| | 43.250 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 3rd Phase: (7 Dragees) | 1.000 mg. | Estriol |
| | 45.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |

EXAMPLE 2

| | (Composition of a Dragee for Each Phase) | |
|---|---|---|
| 1st Phase: (11 Dragees) | 2.000 mg. | Estradiol valerate |
| | 2.000 mg. | Estriol |
| | 42.500 mg. | Lactose |
| | 26.800 mg. | Corn starch |
| | 3.000 mg. | Polyvinylpyrrolidone 25 |
| | 3.600 mg. | Talc |
| | 0.100 mg. | Magnesium stearate |
| | 80.000 mg. | Total weight, supplemented to about 140 mg. with customary sugar mixture. |
| 2nd Phase: (10 Dragees) | 2.000 mg. | Estradiol valerate |
| | 2.000 mg. | Estriol |
| | 0.250 mg. | D-Norgestrel |
| | 42.250 mg. | Lactose |
| | 26.800 mg. | Corn starch |
| | 3.000 mg. | Polyvinylpyrrolidone 25 |
| | 3.600 mg. | Talc |
| | 0.100 mg. | Magnesium stearate |
| | 80.000 mg. | Total weight, supplemented to about 140 mg. with customary sugar mixture. |
| 3rd Phase: (7 Dragees) | 1.000 mg. | Estriol |
| | 45.500 mg. | Lactose |
| | 26.800 mg. | Corn starch |
| | 3.000 mg. | Polyvinylpyrrolidone 25 |
| | 3.600 mg. | Talc |
| | 0.100 mg. | Magnesium stearate |
| | 80.000 mg. | Total weight, supplemented to about 140 mg. with customary sugar mixture. |

EXAMPLE 3

| | (Composition of a Dragee for Each Phase) | |
|---|---|---|
| 1st Phase: (11 Dragees) | 3.000 mg. | Estradiol valerate |
| | 2.000 mg. | Estriol |
| | 41.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 2nd Phase: (10 Dragees) | 3.000 mg. | Estradiol valerate |
| | 2.000 mg. | Estriol |

-continued

| (Composition of a Dragee for Each Phase) | | |
|---|---|---|
| | 2.000 mg. | Norethisterone acetate |
| | 39.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 3rd Phase: (7 Dragees) | 1.000 mg. | Estriol |
| | 45.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |

EXAMPLE 4

| (Composition of a Dragee for Each Phase) | | |
|---|---|---|
| 1st Phase: (11 Dragees) | 4.000 mg. | Estradiol valerate |
| | 2.000 mg. | Estriol |
| | 40.500 mg. | Lactose |
| | 26.800 mg. | Corn starch |
| | 3.000 mg. | Polyvinylpyrrolidone 25 |
| | 3.550 mg. | Talc |
| | 0.150 mg. | Magnesium stearate |
| | 80.000 mg. | Total weight, supplemented to about 140 mg. with customary sugar mixture. |
| 2nd Phase: (10 Dragees) | 4.000 mg. | Estradiol valerate |
| | 2.000 mg. | Estriol |
| | 0.250 mg. | D-Norgestrel |
| | 40.250 mg. | Lactose |
| | 26.800 mg. | Corn starch |
| | 3.000 mg. | Polyvinylpyrrolidone 25 |
| | 3.550 mg. | Talc |
| | 0.150 mg. | Magnesium stearate |
| | 80.000 mg. | Total weight, supplemented to about 140 mg. with customary sugar mixture. |
| 3rd Phase: (7 Dragees) | 2.000 mg. | Estriol |
| | 44.500 mg. | Lactose |
| | 26.800 mg. | Corn starch |
| | 3.000 mg. | Polyvinylpyrrolidone 25 |
| | 3.550 mg. | Talc |
| | 0.150 mg. | Magnesium stearate |
| | 80.000 mg. | Total weight, supplemented to about 140 mg. with customary sugar mixture. |

EXAMPLE 5

| (Composition of a Dragee for Each Phase) | | |
|---|---|---|
| 1st Phase: (11 Dragees) | 0.500 mg. | Estradiol valerate |
| | 4.000 mg. | Estriol |
| | 42.000 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 2nd Phase: (10 Dragees) | 0.500 mg. | Estradiol valerate |
| | 4.000 mg. | Estriol |
| | 1.000 mg. | Cyproterone acetate |
| | 41.000 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 3rd Phase: (7 Dragees) | 2.000 mg. | Estriol |
| | 44.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with |

-continued

| (Composition of a Dragee for Each Phase) | | |
|---|---|---|
| | | customary sugar mixture. |

EXAMPLE 6

| (Composition of a Dragee for Each Phase) | | |
|---|---|---|
| 1st Phase: (11 Dragees) | 1.000 mg. | Estradiol valerate |
| | 4.000 mg. | Estriol |
| | 41.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 2nd Phase: (10 Dragees) | 1.000 mg. | Estradiol valerate |
| | 4.000 mg. | Estriol |
| | 0.250 mg. | D-Norgestrel |
| | 41.250 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 3rd Phase: (7 Dragees) | 2.000 mg. | Estriol |
| | 44.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |

EXAMPLE 7

| (Composition of a Dragee for Each Phase) | | |
|---|---|---|
| 1st Phase: (11 Dragees) | 2.000 mg. | Estradiol valerate |
| | 1.000 mg. | Estriol |
| | 43.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 2nd Phase: (10 Dragees) | 2.000 mg. | Estradiol valerate |
| | 1.000 mg. | Estriol |
| | 0.250 mg. | D-Norgestrel |
| | 43.250 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 3rd Phase: (7 Dragees) | 0.500 mg. | Estriol |
| | 46.000 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |

EXAMPLE 8

| (Composition of a Dragee for Each Phase) | | |
|---|---|---|
| 1st Phase: (11 Dragees) | 1.000 mg. | Estradiol valerate |
| | 2.000 mg. | Estriol |
| | 43.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 2nd Phase: | 1.000 mg. | Estradiol valerate |

| (Composition of a Dragee for Each Phase) | | |
|---|---|---|
| (10 Dragees) | 2.000 mg. | Estriol |
| | 0.250 mg. | D-Norgestrel |
| | 43.250 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |
| 3rd Phase: (7 Dragees) | 46.500 mg. | Lactose |
| | 26.800 mg. | Corn starch |
| | 3.000 mg. | Polyvinylpyrrolidone 25 |
| | 3.700 mg. | Talc |
| | 80.000 mg. | Total weight, supplemented to about 140 mg. with customary sugar mixture. |

The preceding examples can be repeated with similar success by substituting the generically and specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition for the treatment of climacteric disturbances, to be administered in three phases, which comprises:
   for the first phase, 10-12 dosage units of a combination of an estradiol estrogen and an estriol estrogen, approximately in a weight ratio of from 2:1 to 1:8,
   for the second phase, 9-11 dosage units of a combination of an estradiol estrogen and an estriol estrogen, approximately in a weight ratio of from 2:1 to 1:8 and a progestational agent; and
   for the third phase, 6-8 dosage units of an estriol estrogen or a placebo.

2. The composition of claim 1 wherein the ratio of estradiol estrogen to that of estriol estrogen for both the first and second phases is about 1:2.

3. The composition of claim 1 wherein the dosage units are in tablet form.

4. The composition of claim 1 wherein the estriol estrogen is estradiol valerate.

5. The composition of claim 1 wherein the estriol estrogen is estriol.

6. The composition of claim 1 wherein the progestogen is D-norgestrel.

7. The composition of claim 1 wherein the progestogen is norethisterone acetate or cyproterone acetate.

8. The composition of claim 1 wherein the amount of progestational agent in a daily dosage is equivalent in activity to 0.1 - 0.5 mg. of D-norgestrel.

9. The composition of claim 1 wherein the daily dosage of estradiol estrogen is equivalent in activity to 0.5 - 4 mg. of estradiol valerate.

10. The composition of claim 1 wherein the amount of estriol estrogen is equivalent in activity to 0.5 - 8 mg. of estriol.

11. The composition of claim 9 wherein the estradiol estrogen is estradiol valerate.

12. The composition of claim 10 wherein the estriol estrogen is estriol.

13. The composition of claim 8 wherein D-norgestrel is the progestational agent.

14. The composition of claim 8 wherein noretheristerone acetate or cyproterone acetate is the progestational agent.

15. In a method of alleviating the physiological and psychological disturbances of menopause comprising administrating to a female afflicted therewith an amount effective to alleviate those disturbances of an estradiol estrogen and an estriol estrogen, approximately in a weight ratio of 2:1 to 1:8 daily for a first 10-12 days and then daily for the next 9-11 days and thereafter an estriol estrogen or a placebo daily for the next 6-8 days, the improvement which comprises administering a progestogen daily concurrently with the estrogens during said next 9-11 days.

16. The method of claim 15 wherein the ratio of estradiol estrogen to that of estriol estrogen in both the first and second administration phases is about 1:2.

17. The method of claim 15 wherein the amount of estradiol estrogen administered daily is equivalent in activity to 0.5 - 4 mg. of estradiol valerate and the amount of estriol estrogen administered daily is equivalent in activity to 0.5 - 8 mg. of estriol.

18. The method of claim 15 wherein the amount of progestational agent administered daily is equivalent in activity to 0.1 - 0.5 mg. of D-norgestrel.

19. The method of claim 18 wherein the hormone-active agents are administered orally.

20. The method of claim 19 wherein estradiol valerate is the estradiol estrogen and estriol is the estriol estrogen.

21. The method of claim 20 wherein D-norgestrel, norethisterone acetate or cyproterone acetate is the progestogen.

22. A composition comprising an estradiol estrogen and an estriol estrogen in a ratio from 2:1 to 1:8 and a progestational agent.

23. The composition of claim 22 wherein the ratio of estradiol estrogen to that of estriol estrogen is about 1:2.

* * * * *

UNITED STATES PATENT AND TRADEMARK OFFICE
CERTIFICATE OF CORRECTION

PATENT NO. : 4,145,416
DATED : March 20, 1979
INVENTOR(S) : Ursula Lachnit-Fixson et al It is certified that error appears in the above-identified patent and that said Letters Patent are hereby corrected as shown below:

Claim 4, lines 47-48: reads "estriol estrogen"

should read -- estradiol estrogen --.

Signed and Sealed this

Twenty-eighth Day of August 1979

[SEAL]

Attest:

LUTRELLE F. PARKER
*Attesting Officer*    *Acting Commissioner of Patents and Trademarks*